United States Patent
Böing et al.

(10) Patent No.: US 7,526,063 B2
(45) Date of Patent: Apr. 28, 2009

(54) SYSTEM FOR GENERATING, EVALUATING AND DISTRIBUTING COMPUTER-TOMOGRAPHICAL 4D REPRESENTATIONS OF THE HEART OF A PATIENT

(75) Inventors: Dieter Böing, Erlangen (DE); Axel Kuettner, Tübingen (DE); Johann Uebler, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/405,641

(22) Filed: Apr. 18, 2006

(65) Prior Publication Data

US 2006/0245536 A1    Nov. 2, 2006

(30) Foreign Application Priority Data

Apr. 19, 2005    (DE)    ........................ 10-2005-018 067

(51) Int. Cl.
    *A61B 6/00*    (2006.01)
(52) U.S. Cl. .................. 378/8; 378/4; 378/95; 378/901
(58) Field of Classification Search ................ 378/4–12, 378/95, 901
    See application file for complete search history.

(56) References Cited

U.S. PATENT DOCUMENTS

| 6,115,486 | A  | * | 9/2000 | Cantoni ....................... 382/128 |
| 6,408,043 | B1 | * | 6/2002 | Hu et al. ........................ 378/8 |
| 6,426,990 | B1 | * | 7/2002 | Cesmeli .......................... 378/8 |
| 6,526,117 | B1 | * | 2/2003 | Okerlund et al. ............... 378/8 |
| 6,556,695 | B1 | * | 4/2003 | Packer et al. ................. 382/128 |
| 6,628,743 | B1 | * | 9/2003 | Drummond et al. ............ 378/8 |

| 2004/0087853 | A1 | * | 5/2004 | Fujisawa ..................... 600/425 |

(Continued)

FOREIGN PATENT DOCUMENTS

DE    100 63 636 A1    7/2001

(Continued)

OTHER PUBLICATIONS

Vedam et al., Acquiring a Four-dimensional Computed Tomography Dataset Using an External Respiratory Signal, 2003, Physics in Medicine and Biology, 48, 45-62.*

(Continued)

*Primary Examiner*—Edward J Glick
*Assistant Examiner*—Alexander Taningco
(74) *Attorney, Agent, or Firm*—Harness, Dickey & Pierce, P.L.C.

(57) ABSTRACT

A system is disclosed for generating, evaluating and distributing computer-tomographical 4D representations of the heart of a patient. The system includes a cardio CT appliance, where a first low-resolution reconstruction of cardio recordings in a multiplicity of cycle phases of the cardiac cycle and subsequent volume rendering of these cardio recordings for 3D representation and examination of the clarity of motion of the representation in the individual cycle phases are performed. This representation is used to select one or two cycle phases with a relatively reduced or even minimal lack of clarity of motion. High-resolution representations of the heart are reconstructed for these selected one or two cycle phases, with the computation and control unit transmitting only the high-resolution representations of the selected cycle phases with a relatively reduced lack of clarity of motion to the at least one workstation as still images, and the workstation being used to perform the evaluation.

17 Claims, 3 Drawing Sheets

U.S. PATENT DOCUMENTS

2004/0175024 A1* 9/2004 Rasche et al. ............... 382/128
2007/0053482 A1* 3/2007 Kohler et al. .................. 378/8

FOREIGN PATENT DOCUMENTS

WO    WO 2005/008597 A2    1/2005

OTHER PUBLICATIONS

Underberg et al., Four-dimensional CT Scans for Treatment Planning in Stereotactic Radiotherapy for Stage 1 Lung Cancer, 2004, Int. J. Radiation Oncology Biol. Phys., vol. 60., No. 4, pp. 1283-1290.*
Manzke et al., Automatic phase point determination for cardiac CT imaging, Medical Imaging 2004, Proceedings of SPIE, vol. 5370, pp. 690-700.*

* cited by examiner

SYSTEM FOR GENERATING, EVALUATING AND DISTRIBUTING COMPUTER-TOMOGRAPHICAL 4D REPRESENTATIONS OF THE HEART OF A PATIENT

The present application hereby claims priority under 35 U.S.C. §119 on German patent application number DE 10 2005 018 067.1 filed Apr. 19, 2005, the entire contents of which is hereby incorporated herein by reference.

FIELD

The invention generally relates to a system for generating, evaluating and distributing computer-tomographical 4D representations of the heart of a patient. For example, it may relate to one having a CT appliance with at least one beam source which is moved on a spiral path around the patient, at least one detector which detects the absorption of the radiation coming from the beam source, and a control and computation unit which controls the CT appliance and can reconstruct the computer-tomographical 4D representation of the motion of the heart, and at least one separate workstation which is connected to the control and computation unit via a network.

BACKGROUND

Systems are generally known, and today's radiologists first of all reconstruct cardio CT images for all cardiac phases in maximum resolution directly after the data acquisition and then transfer them to a separate workstation for further evaluation. In the case of these multiphase reconstructions, approximately 300 images of the heart are respectively reconstructed on the CT appliance in different sectional planes, that is to say a total of approximately 3000 to 6000 images per examination, normally in 5% to 10% sections of the cardiac phase, and are then transferred to the separate workstation. There is no prior identification of the cardiac phases in which the motion artifacts are smallest. The reconstruction time with today's usual matrix size of 512×512 pixels lasts approximately 5 to 10 minutes and data volumes of approximately 1.5 to 3 GB are obtained which then again require approximately the same time just for transfer via networks at approximately 2 MB/s, today's usual transfer performance in the generally usual DICOM standard.

This may result in unnecessary loading on the clinical networks, with unnecessarily large data volumes being transferred which are not relevant for targeted clinical investigation, e.g. coronary diagnostics. This normally requires only 1 to 2 reconstructions of the cardiac phases. Beside this, a diagnostic statement is slowed down an unreasonable amount for time-critical cases.

SUMMARY

An object of at least one embodiment of the invention is to find a system in which the large data volumes which have been transferred between the CT appliance and the workstation for cardiac examinations to date can be drastically reduced in time in order to allow further processing and diagnostics within an efficient time.

The inventor has recognized that a drastic reduction in the transferred data volumes is possible if the actual CT appliance presents the available data in a manner such that even personnel with little training are able to make a preselection for evaluating relevant data, or that an automatic preselection is made by appropriate image analysis methods, so that ultimately only image and data material which is actually relevant is transmitted to a downstream workstation on which the actual evaluation takes place.

Accordingly, in at least one embodiment, the inventors propose an improved system for generating, evaluating and distributing computer-tomographical 4D representations of the heart of a patient which has a CT appliance having at least one beam source which is moved on a spiral path around the patient, at least one detector which detects the absorption of the radiation coming from the beam source, and a control and computation unit which controls the CT appliance and can reconstruct the computer-tomographical 4D representation of the motion of the heart. Here, the control and computation unit performs a first low-resolution reconstruction of the cardio recordings in a multiplicity of cycle phases of the cardiac cycle and subsequent volume rendering of these cardio recordings for 3D representation and examination of the clarity of motion in the representation in the individual cycle phases, and this representation is used on the control and computation unit to select one or two cycle phases with a relatively reduced or even minimal lack of clarity of motion, and high-resolution representations of the heart are reconstructed for these selected one or two cycle phases. The improved system, in at least one embodiment, also has at least one separate workstation which is connected to the control and computation unit via a network, with the computation and control unit transmitting only the high-resolution representations of the selected cycle phases with low lack of clarity of motion to the at least one workstation as still images, and the workstation being used to perform the evaluation.

In the case of at least one embodiment of the system illustrated above for generating, evaluating and distributing computer-tomographical 4D representations of the heart of a patient, the individual functions can be realized by appropriate integrated programs which are split between the control and computation unit and the at least one workstation according to specific function.

The inventors also propose, in at least one embodiment, that the recordings to be transmitted to the workstation have all other objects which are not used to represent the heart removed from them on the control and computation unit before they are transmitted to the at least one workstation. This firstly improves the evaluation capability of the cardio representations, and secondly this also reduces the workload for the workstation, so that not only is the load on the data transmission paths reduced, but also the necessary computation capacity to be held for the workstation can end up lower.

In addition, the workstation can hold a program which can take the 3D representation of a cycle phase of the heart and generate a sectional image in a plane specified manually on the screen.

In line with a further-improved variant, the workstation can hold a program which, as a result of a click on a coronary artery in the 3D representation of a cycle phase of the heart, marks the entire length of this coronary artery and makes a curved virtual cut along the coronary artery and outputs this cut as a 2D representation on the screen. Thus, the radiologist has the entire path of the coronary artery available in a 2D representation in which a stenosis which might be present can easily be identified without having to produce a multiplicity of sectional planes with great effort.

In line with at least one embodiment of the invention, to produce an optimum representation of the left and right coronary arteries of the heart a respective cardiac phase can also be selected for which the high-resolution reconstruction is performed. That is to say that it is possible to select different cardiac phases, with the respective phase with an optimally small amount of motion being selected for each coronary artery, and hence exactly the images of these phases being transmitted in high resolution from the CT to the workstation for evaluation.

In addition, the optimum cardiac phase for the high-resolution reconstruction can be selected automatically by way of image analysis, or the result of the automatic selection of the optimum cardiac phase can be presented to a user using the control and computation unit, and said user can confirm this selection or change the selection for the high-resolution reconstruction.

To support the evaluation, the control and computation unit can create a low-resolution film sequence of a volume-rendered representation of the cardiac motion and can transmit it to the workstation. As a result, on the one hand, the entire cardiac phase is shown to the evaluating radiologists as a film, but this requires a much smaller volume of data to be transmitted than would be required for fully providing all volume data for the cardiac motion.

To add to this, it is also advantageous to transmit the data required for functional diagnostics in addition to the data required for morphological diagnostics. Even this requires only the actually necessary data to be transmitted, however, without "ballast", within the context of at least one embodiment of the invention. Accordingly, the inventors also propose, in at least one embodiment, that only the control and computation unit is used for automatically calculating the ejection fraction and/or the contractility and/or the myocardial mass of the heart, and only the respective result data are transmitted to the workstation.

In addition, only the control and computation unit can be used for automatically analyzing myocardial wall motions and possibly disturbances therein, and in this case too only the result data can be transmitted to the workstation.

BRIEF DESCRIPTION OF THE DRAWINGS

The invention is described in more detail below using the example embodiments with reference to the figures, where only the features required for understanding the invention are shown. In this case, the following reference symbols are used: 1: computer tomograph; 2: X-ray tube; 3: detector; 4: system axis; 5: ECG line; 6: patient's couch; 7: patient; 8: control line for the contrast agent injector; 9: control and computation unit; 10: control and data line; 11: contrast agent injector; 12: contrast agent line; 13: workstation; 14: network; 21-29: steps in the workflow; 31: marked artery of the heart; $Prg_1$-$Prg_n$: programs on the control and computation unit; $Prg_{n+1}$-$Prg_m$: programs on the workstation.

In the figures, specifically.

DETAILED DESCRIPTION OF THE EXAMPLE EMBODIMENTS

Figure 1:
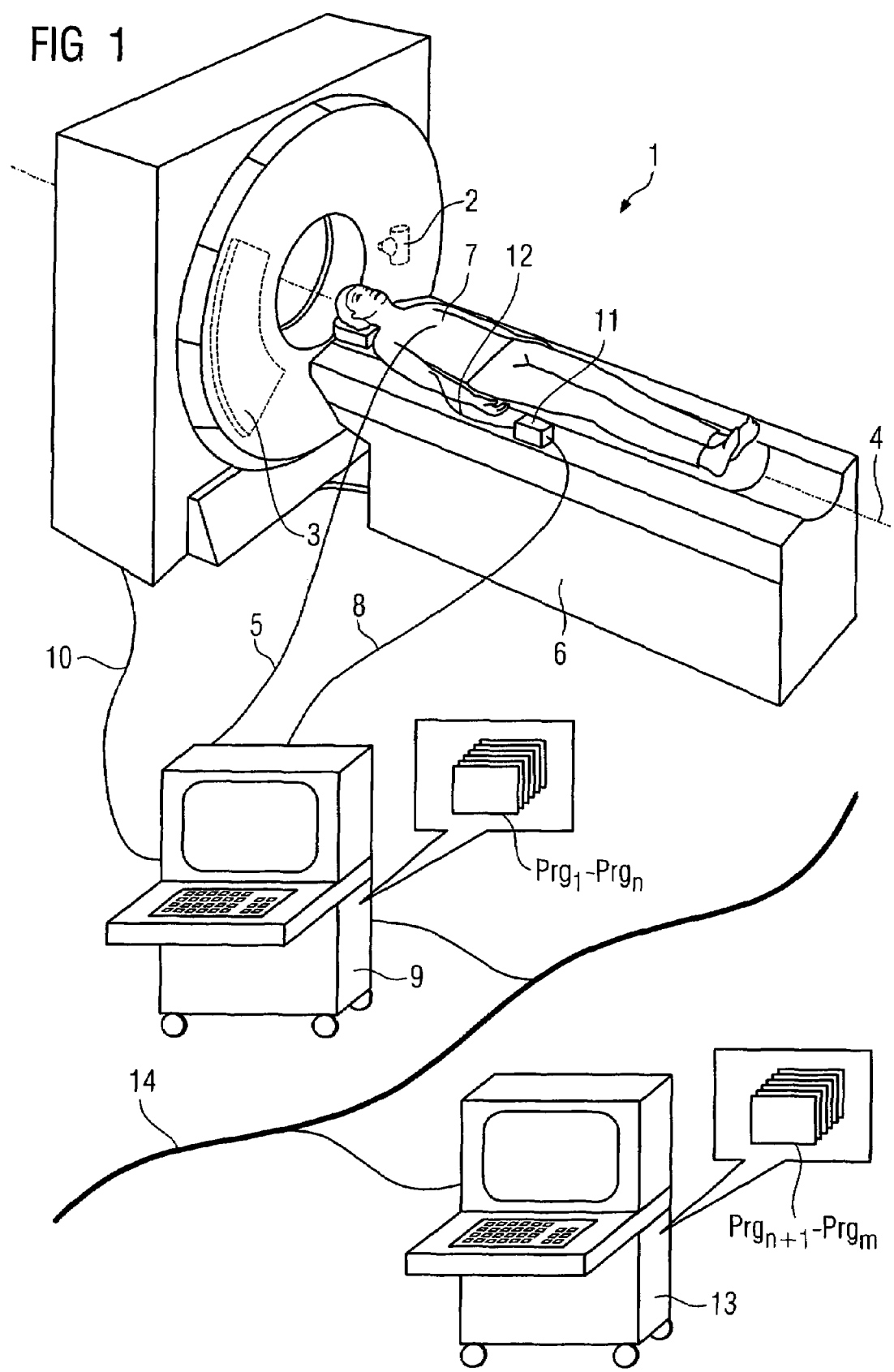
FIG. 1: shows a schematic illustration of a CT with connected network and workstation.

To clarify the inventive system, FIG. 1 shows a schematic illustration of a computer tomograph 1 with a control and computation unit 9 which is connected to a network 14. The CT 1 has at least one X-ray tube 2 and a detector 3 for scanning a patient 7 who is on a patient's couch 6 which can be moved in the direction of the system axis 4. By moving the X-ray tube 2 in a circle and simultaneously moving the patient 7 in a longitudinal direction, a spiraled scan is obtained relative to the patient. The CT is controlled by the control and computation unit 9 via the control and data line 10, this line 10 also being used to transmit the detector output data from the detector 3 to the control and computation unit 9.

To perform a cardio scan, information about the cardiac activity, particularly about the current cardiac cycle phase correlated to the detector output data, is also required. This information can be obtained using the ECG line 5 shown and an ECG appliance integrated in the control and computation unit, for example. In addition, the control and computation unit 9 also controls the flow of contrast agent via the control line 8, which is connected to a contrast agent injector 11 which injects contrast agent into the blood circulation of the patient 7 via the contrast agent line 12 at the desired time and at the desired flow rate.

The programs $Prg_1$-$Prg_n$ required for operating the CT and particularly for evaluating the measured data obtained are stored in the data store in the control and computation unit 9 and can be called when required. Hence, following the scan on the control and computation unit 9, on which all the detector output data are also stored, at least one embodiment of the invention starts the appropriate programs for reconstruction at reduced resolution, preselection of the correct cardiac phase to be observed and reconstruction of the image data from these selected cardiac phases at high resolution, with function-diagnostic evaluations also being able to be performed here in addition.

Only the data which are relevant to the evaluation are then transmitted to a connected workstation 13 via the network 14, so that the loading on the network 14 and also the computation time required for this on the control and computation unit 9 and the workstation 13 are kept down. This is where the actual evaluation of the data previously considered to be relevant is made by medical personnel. This evaluation is supported by the auxiliary means which are stored in the programs $Prg_{n+1}$-$Prg_m$.

Figure 2:
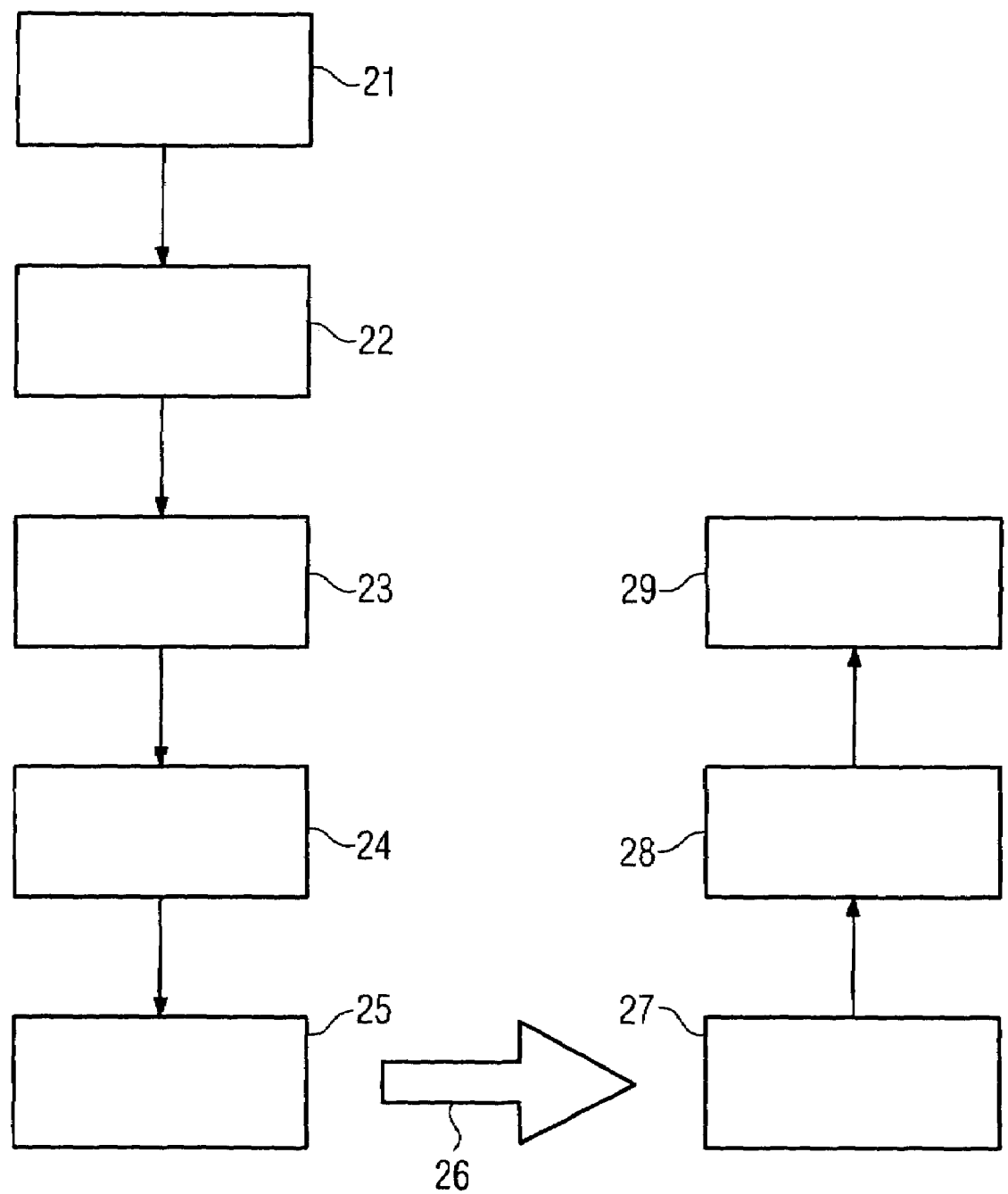
FIG. 2: shows an example of a workflow based on at least one embodiment of the invention.

FIG. 2 shows a coarse overview of the inventive workflow. The workflow starts at step 21, in which the examination planning is carried out by ascertaining the scan parameters, such as dosage, feed speed, flow of contrast agent and creation of a topogram. Next, the actual spiral scan is performed in step 22, followed by the reconstruction of the image data at low resolution 23 over all cardiac phases.

Step 24 represents the selection of the evaluation-related cardiac phases using the low-resolution images reconstructed to date and the volume-rendered 3D representations of the cardiac phases which have been calculated therefrom. In step 25, those image data from the selected cardiac phases which are relevant to the morphological diagnostics are reconstructed at high resolution, and evaluations relevant to the functional diagnostics are optionally also performed. Next, only the data which are relevant to the evaluation are transmitted to a workstation associated with the evaluating doctor via the network in step 26.

The workstation now performs the morphological evaluation in step 27 and optionally the function-diagnostic evaluation in step 28, with appropriate documentation for the findings being able to be created in step 29 and possibly being able to be forwarded to or stored at other locations.

The individual steps of the workflow are described again in more detail below:

In line with at least one embodiment of the invention, cardio examination protocols are intended to provide a maximum level of automation in future and therefore to trigger all the necessary cycles, inter alia, automatically. In this context, the evaluating radiologist will serve as control entity for the automatically created images relevant to findings. To this end, it is also necessary for just these relevant data to be made available to him on the workstation, and non-relevant data do not need to be transferred, which also results in the evaluation time being optimized.

In line with the ideas of the inventors, in at least one embodiment, an example cardio examination using an ECG signal therefore proceeds as follows:

When the patient has been positioned and the ECG electrodes have been attached, the ECG signal is displayed on a CT control monitor. To save dosage, a dosage plateau is defined which adapts itself to the heart rate. This dosage plateau is embedded between the two R peaks of the ECG centrally over the optimum cardiac phase expected for the detected heart rate, and can additionally be defined using a percentage setting, distance to the R-peak before/after the systole. This distance is approximately 10% before and after the peak of the R-peak. If the heart rate now changes during the administration of contrast agent before the start of radiation, usually becoming higher, the plateau is dynamically adjusted.

An overview recording (topogram) is then taken. The topogram is the basis for planning the cardio examination. When the examination region has been anatomically adjusted, a CT spiral scan is started.

When the spiral scan has ended, the axial image stack is presented beside the topogram, and a better overview and assessment can be obtained by switching to a 3D or 4D representation of the heart volume. This visually simplifies the selection of the morphologically relevant cardiac phases. A "multiple curved thin MIP" (curved MIP region reconstruction along a coronary vessel) allows improved visualization of the vessel which the radiologist wishes to evaluate.

Directly after the measurement, an overview reconstruction is automatically performed in the background over all cardiac phases in order to allow the 4D representation. The parameters for the overview reconstruction, such as phase start, increment, number of phases, can be configured by the user individually, e.g. 0-100% in 5% increments.

The data obtained from the spiral acquisition can be visualized for the user in 3D or 4D representation directly after the examination.

In at least one embodiment, it is advantageous if all orientations which are relevant for optimum consideration or for evaluation can be selected in the form of predefined orientations.

Directly after the data acquisition, presegmentation of the cardiac image data can take place, which allows the short cardiac axis to be found automatically. Other orientations, such as LAO and RAO (left/right anterior oblique), can be predefined and stored and automatically presented to the user. The orientations can be adjusted by the user as required. They are used inter alia for identifying the optimum cardiac phase and evaluating disturbances to the motion of the wall.

The evaluation-related data for coronary and functional diagnostics make different quality demands on the CT data. For functional diagnostics, a reduced image matrix is sufficient, for example a matrix based on the "gold standard" with $256^2$ pixels, whereas coronary diagnostics require the maximum image quality to be provided. In line with at least one embodiment of the invention, a maximum data reduction is therefore made on the actual CT appliance by way of the automatic identification of the optimum cardiac phases. All phases in which systolic motion artifacts cause a disturbance, for example, are excluded from the data export as not being relevant to findings, or are used exclusively for functional diagnostics with a smaller matrix size.

The desired cardiac phases, e.g. at 5% distances with 20 cardiac phases, are reconstructed, without user interaction, automatically at reduced resolution, for example in a $256^2$ image matrix. Inherently known algorithms or manual interactions allow the phases to be identified in which the motion artifacts in the coronary vessels are smallest. The user should optionally have manual and automatic identification of the optimum phases available.

In the case of manual identification of the optimum phase(s), after the examination the user will check the ECG to identify possible irregularities, such as extra systoles or greatly varying heart rate. He may need to adapt the reconstruction to the ECG and/or to edit the ECG signal in suitable fashion. In the case of a patient with a regular heartbeat and a heart rate which is not excessive, the experienced radiologist can use his empirical values to set the optimum phase manually and to reconstruct the optimum cardiac phase without software support. A user-definable mapping table can be used to define the optimum phases for different heart rates. This mapping table associates optimum ECG phases with different heart rates.

Selection of the optimum cardiac phase for the respective problem will be made possible using a "phase viewer". The user can use this to display all the phases from the overview reconstruction. The simplest and clearest method is selection using a volume-rendered 3D or 4D representation of the heart.

Figure 3:
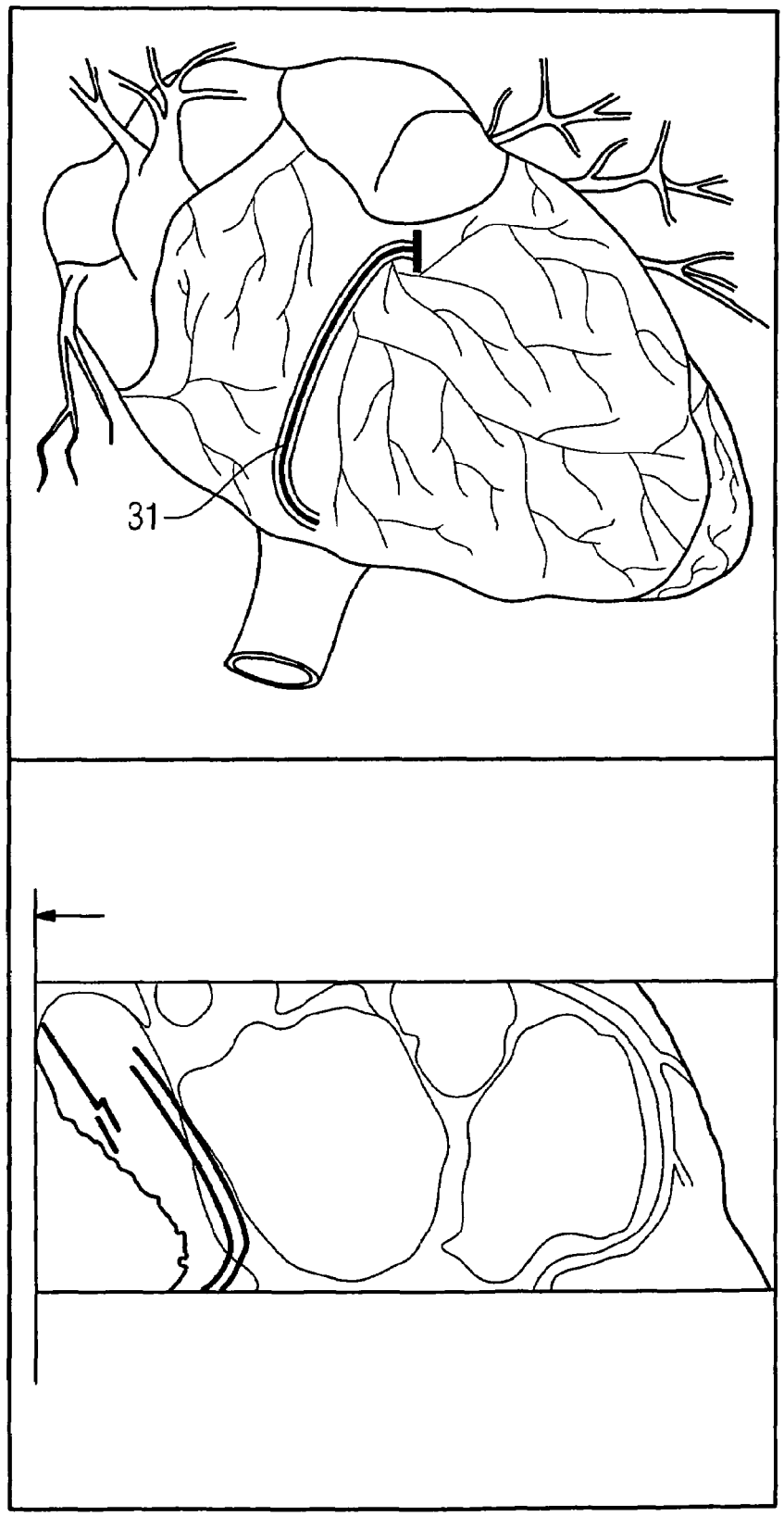
FIG. 3: shows an illustration of a volume-rendered view of the heart with a "curved cut" view of a selected artery.

In this case, it is extremely useful to show the heart without an interfering environment, such as rib bones. A representation of this type is shown in the top segment of FIG. 3. In addition, predefined orientations (LAO, RAO) are intended to simplify the view of the coronary arteries. In this case, manual marking 31 of a coronary artery can advantageously trigger automatic production of a "curved cut" along the selected coronary artery, and the sectional representation of this coronary artery can be shown on the screen beside the 3D representation of the heart. Such a view is shown in FIG. 3, where the bottom segment of FIG. 3 shows a typical "curved cut" representation as a 2D sectional image. As an alternative to this, clicking in the coronary artery could define a "seed point", which allows the coronary artery to be found automatically and allows the "curved cut" to be routed as appropriate.

Coronary diagnostics normally require 1 to 2 cardiac phases, which may be different for the left and right coronary arteries of the heart (LCA, RCA). However, it is also possible to select three or more phases from the multiplicity of those available for diagnostics. The phases vary depending on the heart rate. The optimum cardiac phases, depending on the heart rate, can be stored in a mapping table, shown below by way of example.

|  | Heart beats per minute | | | | |
| --- | --- | --- | --- | --- | --- |
|  | <60 | 60-70 | 75-80 | 80-90 | >90 |
| Optimum phase (empirical values) | 65% | 60% | 35% | 25% | 15-20% |

Alternatively, automatic identification of the optimum phase(s) is proposed. In this case, the system is intended to present the optimum phases for the coronary arteries to the radiologist or assistant automatically upon request. Inherently known image analysis methods are then intended to identify the phases in which no motion artifacts can be seen along the left and right coronary vessels. The user can accept this proposal or can select other phases manually, as described above.

To avoid further examinations and beam exposure for the patient, automatic functional diagnostics can also be performed from the CT data records which are already available for the morphological diagnostics, and can be made available to the evaluating doctor. Accordingly, automatic calculation of the ejection fraction (EF) or contractility (time function curve) or automatic determination of the myocardial mass and also analysis of disturbances to the wall motion can be carried out with the image sequences already calculated at reduced resolution on the CT, and can be presented to the evaluating doctor in the manner examined previously.

Hence, for every cardiac examination which was initially planned for coronary diagnostics, the user is presented with results from the functional diagnostics, which are today performed only optionally for reasons of time, with no additional effort. From a clinical point of view, functional diagnostics are an integral part of cardiac diagnostics and are frequently carried out in conventional coronary angiography using additional contrast agent and an additional beam exposure. These diagnostics provide information about whether any constriction of the coronary arteries which is present is already causing a disturbance in the wall motion or a global reduced output from the heart. The proposed method allows the data to be provided, both for the functional cardiological evaluation and for the morphological diagnostics for the coronary vessels, in an optimally combined and hence extremely efficient way.

The reconstructions with the optimum cardiac phases, as identified by the system or user, can also be automatically loaded into a manufacturer-specific cardio application so that morphological questions can be answered. Alternatively, these data generated in this way can be made available to any post-processing and findings workstations independently of manufacturer.

In addition, preliminary findings created by a cardio application can reference all images which provide evaluation-related statements. This can then be documented in a pre-structured report, for example. This report can be transferred by network in the same way as any image. Alternatively, the report generated in this manner may be incorporated into manufacturer independent systems as a text module. These report documents need to be initialed by the evaluating radiologists, and possibly corrected, in a further step.

This integration of the functionalities important to cardiac diagnostics provides the radiologist with routines, on the actual CT scanner, which significantly simplify the routine performance of CT examinations. The evaluation-related data can thus be automatically ascertained to a very large extent using integrated SW tools. Besides the time saving, this also achieves better clinical results.

On the CT scanner of at least one embodiment, improved or even maximum data reduction is achieved by identifying the optimum cardiac phases. All phases in which, by way of example, systolic motion artifacts cause a disturbance are excluded from the time-consuming reconstruction and hence also from the data export as not being relevant to findings, or are used exclusively for functional diagnostics with a smaller matrix size.

The advantages over the conventional method, in at least one embodiment, can be summarized into three main points:

time saving when calculating all findings-related images as a result of automatic software support with intelligent selection of the images and their image resolution for evaluation/sending to other workstations.

improvement of the morphological diagnosis, since the evaluating radiologist is provided with all the necessary images for the diagnostics.

new, extended diagnoses are permitted, since the functional diagnostics are being made accessible as a new evaluation entity for everyday clinical work.

Overall, at least one embodiment of the invention therefore proposes a system for generating, evaluating and distributing computer-tomographical 4D representations of the heart of a patient using a cardio CT appliance in a manner optimized for data transfer, where the control and computation unit of the CT performs a first low-resolution reconstruction of cardio recordings in a multiplicity of cycle phases of the cardiac cycle and subsequent volume rendering of these cardio recordings for 3D representation and examination of the clarity of motion of the representation in the individual cycle phases, this representation is used to select one or two cycle phases with a relatively reduced or even minimal lack of clarity of motion, and high-resolution representations of the heart are reconstructed for these selected one or two cycle phases, with the computation and control unit transmitting only the high-resolution representations of the selected cycle phases with low lack of clarity of motion to the at least one workstation as still images, and the workstation being used to perform the evaluation.

It goes without saying that the features of the invention which are cited above can be used not only in the respectively indicated combination, but also in other combinations or on their own, without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for generating, evaluating and distributing computer-tomographical 4D representations of the heart of a patient, comprising:

at least one workstation configured to perform an evaluation of the patient; and a CT appliance including at least one beam source, at least one detector, and a control and computation unit connected to the at least one workstation via a network, the at least one beam source configured to move on a spiral path around the patient, the at least one detector configured to detect absorption of radiation from the beam source, the control and computation unit configured to control the CT appliance, reconstruct the computer-tomographical 4D representation of the motion of the heart, perform a first low-resolution reconstruction of the cardio recordings in a multiplicity of cycle phases of the cardiac cycle, perform volume rendering of these cardio recordings for 3D representation and examination of the clarity of motion in the representation in the individual cycle phases, select one or two cycle phases with a relatively reduced lack of clarity of motion, reconstruct high-resolution representations of the heart for the selected one or two cycle phases, and transmit only the high-resolution representations of the selected cycle phases with a relatively reduced lack of clarity of motion to the at least one workstation as still images.

2. The system as claimed in claim 1, wherein the control and computation unit is further configured to remove all other objects which are not used to represent the heart before transmitting the still images to the at least one workstation.

3. The system as claimed in claim 1, wherein the at least one workstation includes a screen and is configured to take the 3D representation of a cycle phase of the heart received as a still image from the control and computation unit and generate a sectional image in a plane specified manually on the screen.

4. The system as claimed in claim 3, wherein the at least one workstation is further configured to receive a user input of a click on a coronary artery in the 3D representation of a cycle phase of the heart, mark the entire length of this coronary artery and make a curved virtual cut along the coronary artery and outputs the curved virtual cut as a 2D representation on the screen.

5. The system as claimed in claim 1, wherein, the control and computation unit selects a respective cardiac phase for which the high-resolution reconstruction is performed to produce an improved representation of the left and right coronary arteries of the heart.

6. The system as claimed in claim 5, wherein the control and computation unit selects the respective cardiac phase for high-resolution reconstruction automatically by image analysis.

7. The system as claimed in claim 6, wherein the control and computation unit includes a display and a result of the automatic selection is presented to a user on the display, and said user at least one of confirms the selection and changes the selection for the high-resolution reconstruction.

8. The system as claimed in claim 1, wherein the control and computation unit is further configured to create a low-resolution film sequence of a volume-rendered representation of cardiac motion and transmit the low-resolution film sequence of the volume-rendered representation to the at least one workstation.

9. The system as claimed in claim 1, wherein only the control and computation unit is configured to automatically calculate an ejection fraction of the heart, and result data are transmitted to the at least one workstation.

10. The system as claimed in claim 1, wherein only the control and computation unit is configured to automatically calculate a contractility of the heart, and result data are transmitted to the at least one workstation.

11. The system as claimed in claim 1, wherein only the control and computation unit is configured to automatically calculate a myocardial mass, and result data are transmitted to the at least one workstation.

12. The system as claimed in claim 1, wherein only the control and computation unit is configured to automatically analyze myocardial wall motions and possible disturbances therein, and result data are transmitted to the at least one workstation.

13. The system as claimed in claim 2, wherein the at least one workstation includes a screen and is configured to take the 3D representation of a cycle phase of the heart received as a still image from the control and computation unit and generate a sectional image in a plane specified manually on the screen.

14. The system as claimed in claim 1, wherein the at least one workstation is further configured to receive a user input of a click on a coronary artery in the 3D representation of a cycle phase of the heart, mark the entire length of this coronary artery and make a curved virtual cut along the coronary artery and outputs the curved virtual cut as a 2D representation on the screen.

15. A system for generating, evaluating and distributing computer-tomographical 4D representations of the heart of a patient, comprising:
means for detecting absorption of radiation coming from a beam source;
means for performing a first low-resolution reconstruction of the cardio recordings in a multiplicity of cycle phases of the cardiac cycle; means for a subsequent volume rendering of these cardio recordings for 3D representation and examination of the clarity of motion in the representation in the individual cycle phases;
means for using the representation to select one or two cycle phases with a relatively reduced lack of clarity of motion, with high-resolution representations of the heart being reconstructed for these selected one or two cycle phases; and
means for transmitting only the high-resolution representations of the selected cycle phases with a relatively reduced lack of clarity of motion to the at least one workstation as still images.

16. The system as claimed in claim 15, further comprising:
means for removing all other objects which are not used to represent the heart before the means from transmitting transmits the still images.

17. A computer readable medium storing executable instruction, which when executed by a control and computation unit, causes the control and computation unit to perform a method comprising:
performing a first low-resolution reconstruction of cardio recordings in a multiplicity of cycle phases of the cardiac cycle;
subsequent volume rendering of the cardio recordings for 3D representation and examination of the clarity of motion in the representation in the individual cycle phases;
using the 3D representation to select one or two cycle phases with a relatively reduced lack of clarity of motion, with high-resolution representations of the heart being reconstructed for these selected one or two cycle phases; and
transmitting only the high-resolution representations of the selected cycle phases with a relatively reduced lack of clarity of motion to at least one workstation over a network as still images.

* * * * *